United States Patent [19]

Eaddy, III

[11] Patent Number: 4,578,522
[45] Date of Patent: Mar. 25, 1986

[54] BIARYL ALDEHYDE

[76] Inventor: John F. Eaddy, III, Rte. 12, Box 127-A, Chapel Hill, N.C. 27514

[21] Appl. No.: 650,981

[22] Filed: Sep. 14, 1984

Related U.S. Application Data

[60] Division of Ser. No. 529,767, Aug. 31, 1983, abandoned, which is a continuation of Ser. No. 371,581, Apr. 26, 1982, abandoned.

[51] Int. Cl.$^4$ .............................................. C07C 47/55
[52] U.S. Cl. ..................... 568/425; 560/76; 560/80; 556/21; 562/457; 562/459; 562/462; 562/466; 562/467; 562/469; 562/490; 562/492
[58] Field of Search .......................................... 568/425

[56] References Cited

FOREIGN PATENT DOCUMENTS 0059983 9/1982 European Pat. Off. .

OTHER PUBLICATIONS

Chemical Abstracts, 98(13) 106980h (1982).
Calvin et al, J. Chem. Soc., pp. 2008-2016 (1960).
Fitton et al, Chem. Comm., p. 6 (1968); p. 370 (1969).
Rosevear et al, J. Chem. Soc. (A) p. 164 (1968).
Mukhedkar et al, J. Chem. Soc. (A) p. 3023 (1969).
Calvin et al, Canadian J. Chem., 45, pp. 301-302 (1967).

Primary Examiner—Bernard Helfin
Attorney, Agent, or Firm—Donald Brown

[57] ABSTRACT

This invention relates to a method of synthesis of certain substituted carboxylic acids useful in lowering serum triglyceride and total cholesterol levels in mammals (including man) represented by the general formula I:

$$Ar^1-Ar^2 \qquad (I)$$

wherein
Ar$^1$ is selected from

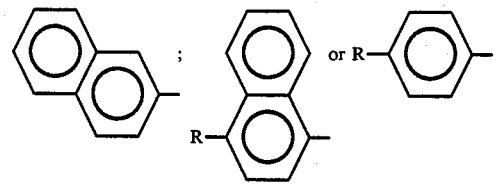

Ar$^2$ is selected from

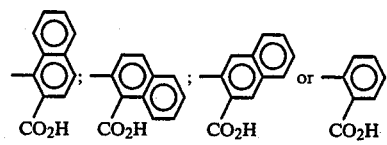

and R is selected from C$_{1-5}$alkyl, halogen, perhalo-C$_{1-4}$alkyl, C$_{1-4}$alkoxy, phenyl, C$_{1-4}$acyl, C$_{1-6}$alkoxycarbonyl, amino or hydroxy.

1 Claim, No Drawings

BIARYL ALDEHYDE

This application is a division of application Ser. No. 529,767, filed Aug. 31, 1983, which is a continuation of Ser. No. 371,581, filed Apr. 26, 1982, both now abandoned.

The present invention relates to derivatives of benzoic acid, to pharmaceutical formulations containing them, to processes for their preparation and to the use thereof in human and veterinary medicine. More specifically the invention relates to 2-(substituted phenyl)-benzoic acids and their use in the control or lowering of blood lipids.

Atherosclerosis is a pathological condition which is a major cause of the occlusive vascular diseases resulting in myocardial infarcation and stroke. This condition is associated with a deposition of blood lipids in the wall of major arteries and is known to occur more frequently in subjects whose blood lipids levels are elevated from established norms. The distribution of lipids in the various lipoprotein components of blood determines the degree of risk/benefit of these materials. High levels of cholesterol in the "low" and "very-low" density lipoprotein are associated with enhanced risk of atherosclerotic coronary artery disease while high levels of the "high-density" lipoprotein-cholesterol of are associated with reduced risks of this disease. Elevation in blood triglyceride levels has also been implicated as a factor which increases the risk developing these vascular diseases. The strong association between the elevation of specific components of blood lipids and these major cardiovascular diseases has led to attempts to control blood lipid levels by management of diet and through drug intervention. It has been found that certain compounds, those of formula (I) below, are effective in reducing the amount of these lipoprotein components in blood which have been associated with atherosclerosis.

The invention accordingly provides, in a first aspect, compounds of formula (I) below, together with pharmaceutically acceptable salts thereof for use in human and veterinary medicine.

Compounds of formula (I) are $$Ar^1-Ar^2 \quad (I)$$

wherein:
$Ar^1$ is selected from

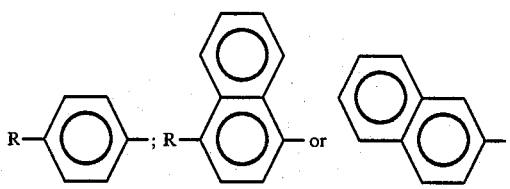

$Ar^2$ is selected from

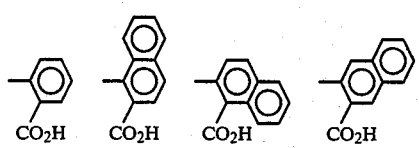

and R is selected from $C_{1-5}$alkyl, halogen, perhalo-$C_{1-4}$alkyl, (such as trihalomethyl), $C_{1-4}$alkoxy, phenyl, $C_{1-4}$acyl, $C_{1-6}$alkoxy carbonyl, amino or hydroxy,
and pharmaceutically acceptable salts thereof.

Preferred compounds within the scope of formula (I) are those of formula (IA) or (IB)

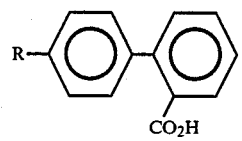

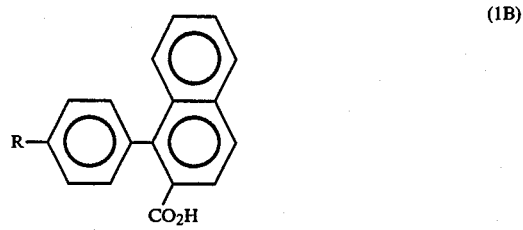

wherein R is as defined above

Preferably R is selected from $C_{1-5}$alkyl, halogen, $C_{1-4}$alkoxy, phenyl or trihalomethyl. In particular compounds in which R is selected from $C_{2-5}$alkyl or trihalomethyl have been found to have activity of or greater than the standard anti-lipidemic compound clofibrate.

Specific compounds of formula I include:
2-(4-Trifluoromethylphenyl)-benzoic acid;
2-(4-Methylphenyl)-benzoic acid;
2-(4-Ethylphenyl)-benzoic acid;
2-(4-iso-Propylphenyl)-benzoic acid;
2-(4-n-Butylphenyl)-benzoic acid;
2-(4-Fluorophenyl)-benzoic acid;
2-(4-Bromophenyl)-benzoic acid;
2-(4-(Chlorophenyl)-benzoic acid;
2-(4-Methoxyphenyl)-benzoic acid;
2-(4-Biphenyl)-benzoic acid.
2-(2-Naphthyl)-benzoic acid;
1-(4-Ethylphenyl)-2-naphthoic acid; and
1-(4-Trifluoromethylphenyl)-2-naphthoic acid.

The most preferred compound of formula (I) is 2-(4-trifluoromethylphenyl)-benzoic acid. Suitable pharmaceutically acceptable acid addition salts include, for example, those derived from the alkali metals (such as sodium or potassium) or alkaline earth metals (such as calcium or magnesium) and ammonium salts (such as $NR_4^+$ wherein R is hydrogen or $C_{1-4}$alkyl, eg $NH_4^+$).

Certain of the compounds of formula (I) have been genericly disclosed in the literature (U.S. Pat. No. 4,242,121) and a number of the compounds specifically disclosed, see for example, J. Chem. Soc. (C), 1968, 848 et. seq. However, there was no teaching or suggestion that the compounds exhibited pharmacological activity.

The compounds of formula (I) are useful in the treatment or prophylaxis of any condition in which the underlying etiology is associated with elevated blood lipid levels. Thus the compounds of formula (I) are useful in the treatment or prophylaxis of atherosclerosis, occlusive vascular diseases and for the reduction or control of levels of blood lipids such as the triglycerides and cholesterol.

The amount of active compound required for use in the above conditions will vary both with the route of administration, the condition under treatment and the mammal undergoing treatment, and is ultimately at the discretion of the physician. A suitable oral dose of the active compound for a mammal is in the range of from 1 to 40 mg per kilogram body weight per day; preferably in the range of 2 to 10 mg/kg bodyweight, a typical dose for a human recipient being about 4 mg/kg bodyweight per day. The desired dose is preferably presented as from one to three sub-doses administered at appropriate intervals throughout the day. Where two sub-doses are employed, each will preferably lie in the range of from 1 to 100 mg/kg bodyweight; a typical sub-dose for a human recipient being about 2 mg/kg bodyweight.

While it is possible that the compounds of formula (I) may be administered as the raw chemical it is preferable to present the active ingredient as a pharmaceutical or veterinary formulation.

Pharmaceutical formulations comprise the active compounds together with one or more pharmaceutically acceptable carriers therefor and optionally other therapeutic and/or prophylactic ingredients. The carrier(s) must be 'acceptable' in the sense of being compatible with the other ingredients of the formula and not deleterious to the recipient thereof.

The invention thus provides in a further aspect a pharmaceutical formulation comprising a compound of formula (I) or a pharmaceutically acceptable salt thereof together with a pharmaceutically acceptable carrier therefor. The active compound(s) may conveniently be presented (as a pharmaceutical formulation) in unit dosage form. A convenient unit dose formulation contains the active ingredient compound(s) in an amount of from 1 to 10 mg.

Pharmaceutical formulations include those suitable for oral, rectal or parenteral (including intramuscular and intravenous) administration, although oral is the preferred route. The formulations may, where appropriate, be conveniently presented in discrete dosage units and may be prepared by any of the methods well known in the art of pharmacy. All methods include the step of bringing into association the active compound with liquid carriers or finely divided solid carriers of both and then, if necessary, shaping the product into the desired formulation.

There is thus provided in a further aspect a method for the preparation of a pharmaceutical formulation comprising a compound of formula I (or a pharmaceutically acceptable salt thereof) together with a pharmaceutically acceptable carrier therefor, which method comprises bringing into association the active compound of formula (I) and the carrier therefor.

Pharmaceutical formulations suitable for oral administration wherein the carrier is a solid are most preferably presented as unit dose formulations such as boluses, capsules, cachets or tablets each containing a predetermined amount of the active ingredient. A tablet may be made of compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating, surface active or dispersing agent. Moulded tablets may be made by moulding an inert liquid diluent. Tablets may be optionally coated and, if uncoated, may be optionally scored. Capsules may be prepared by filling the active compound, either alone or in admixture with one or more accessory ingredients, into the capsule cases and then sealing them in the usual manner. Cachets are analogous to capsules wherein the active ingredient together with any accessory ingredient(s) is sealed in a rice paper envelope.

Pharmaceutical formulations suitable for oral administration wherein the carrier is a liquid may be presented as a solution or a suspension in an aqueous liquid or a non-aqueous liquid, or as an oil-in-water or water-in-oil liquid emulsion.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Pharmaceutical formulations suitable for parenteral administration include sterile solutions or suspensions of the active compound in aqueous or oleaginous vehicles. Such preparations are conveniently presented in unit dose or multidose containers which are sealed after introduction of the formulation until required for use.

It should be understood that in addition to the aforementioned carrier ingredients the pharmceutical formulations described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Compounds of formula (I) and their salts may be prepared by any method well known in the art for preparation of compounds of analogous structure. For example, Compounds of formula (I) may be prepared from a compound of formula (III)

 (III)

wherein $Ar^1$ is as defined in formula (I) above; $Ar^3$ is

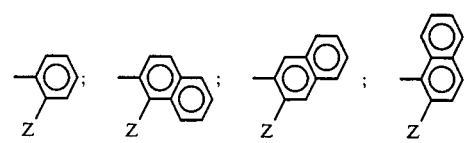

and Z is a protected carboxylic acid group or a precursor of a carboxylic acid group, for example an ester, orthoester, amide, protected aldehyde, protected ketones, an oxazoline residue, for example

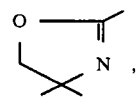

by conversion of the group Z to the group COOH by appropriate means, for example hydrolysis or oxidation. Compounds of formula (III) may be prepared by methods known in the art for the preparation of such compounds. Additionally compounds of formula (III) may be prepared by reaction of a compounds of formula (IV) with a compound of formula (V)

 (IV)

 (V)

wherein M is a metal, such as lithium or MgX, X is halogen (especially chloro or bromo) and $Ar^1$ and $Ar^3$ are as defined above.

The compounds of formula (III) wherein Z is an oxazoline residue may be prepared by reaction of a compound of formula (VI) with a compound of formula (VII)

 (VI)

 (VII)

wherein M and $Ar^1$ are as defined above, and $Ar^3$ is as defined above except that Z is only oxazoline.

Compounds of formula (IV) or formula (VI) are prepared from the corresponding halo, e.g. bromo, compound by the well known method of preparing Grignard reagents. The compound of formula (VII) is prepared from the corresponding acid by the method of Meyers et al., *JACS*, 97, 7383 (1975).

Compounds of formula (I) may also be prepared by reduction of a compound of formula (VIII)

 (VIII)

wherein $Ar^2$ is as defined in formula (I) above, $Ar^4$ is

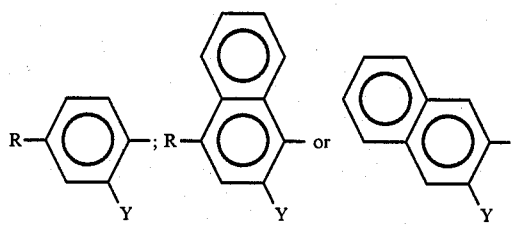

and Y is $-N_2^+X^-$ where $X^-$ is an anion (eg. $Cl^-$).

Compounds of formula (VIII) may be prepared from the corresponding amine, i.e. where Y in formula (VIII) is $-NH_2$. These amines may in turn be prepared via the Schmidt reaction using such agents as hydrogen azide from the appropriate 9-fluoronone derivative.

Compounds of formula (I) can be synthesised from compounds of formula (IX)

 (IX)

wherein $Ar^1$ is as defined in formula (I) above and $Ar^5$ is

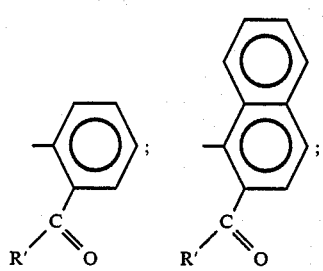

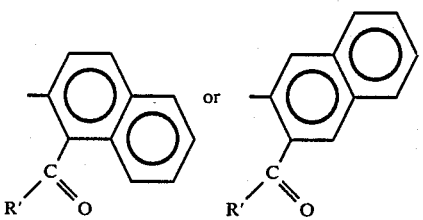

and R' is $C_{1-4}$alkyl or hydrogen by selective oxidation with such agents as hypochlorite or permanganate. Compounds of formula (IX) can be prepared by Friedel-Craft acylation of compounds of formula (X)

 (X)

where $Ar^1$ is as defined above and $Ar^6$ is phenyl, or 1,2 or 3-naphthyl.

Yet another method for the synthesis of compounds of formula (I) involves treating compounds of formula (XI) with $CO_2$. Compounds of formula (XI) may be prepared by reaction of compounds of formula (XII) with magnesium in an etherial solvent such as diethyl ether.

 (XI)

 (XII)

wherein $Ar^9$ and $Ar^{10}$ are:

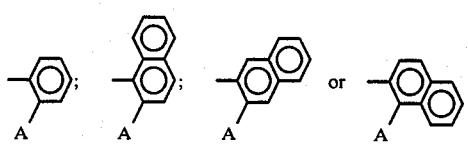

For $Ar^9$ A=X; For $Ar^{10}$ A=MgX;
X is halogen (such as chloro); and
$Ar^1$ is as defined above.

As indicated above certain of the compounds of formula (I) are novel and thus there is provided in a further aspect compounds of formula (II), within the scope of formula (I),

 (II)

in which
$Ar^7$ is selected from

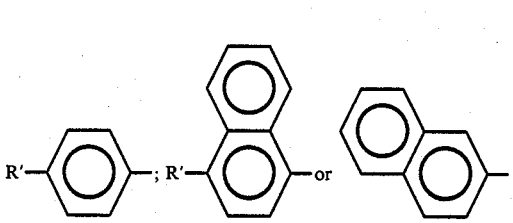

$Ar^8$ is selected from

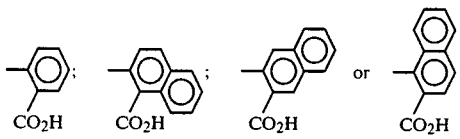

and R[1] is $C_{2-5}$alkyl, perfluoro $C_{1-4}$alkyl (eg trifluoromethyl) or phenyl; and pharmaceutically acceptable salts thereof.

Preferred compounds of formula (II) are those of formula (IIA) or (IIB)

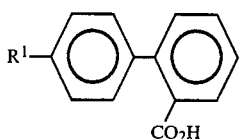 (IIA)

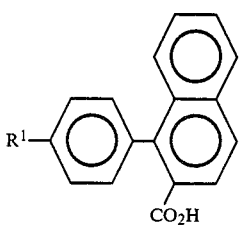 (IIB)

wherein R[1] is as defined above.

Preferred compounds of formula (II) include:
2-(4-Trifluoromethylphenyl)-benzoic acid;
2-(4-Ethylphenyl)-benzoic acid;
2-(4-isoPropylphenyl)-benzoic acid;
2-(4-n-Butylphenyl)-benzoic acid;
2-(4-t-Butylphenyl)-benzoic acid;
2-(4-Biphenyl)-benzoic acid;
1-(4-Trifluoromethylphenyl)-2-naphthoic acid;
1-(4-Ethylphenyl)-2-naphthoic acid; and
2-(2-Naphthyl)-benzoic acid.

The most preferred compound of formula (II) is 2-(4-trifluoromethylphenyl)-benzoic acid.

The following examples illustrate the present invention:

EXAMPLE 1

Preparation of 4'-(Trifluoromethyl)-2-biphenyl carboxylic acid a. Preparation of 2-(4,4-Dimethyl-2-oxazolin-2-yl)-4'-trifluoromethylbiphenyl A mechanically stirred solution of magnesium turnings (5.1 g, 0.21 mole) Mallinckrodt, for Grignards reaction, and 2-(2-methoxyphenyl)-4,4dimethyl-2-oxazoline (41 g, 0.2 mole) in 50 mL dry tetrahydrofuran under nitrogen was prepared. To this was added a crystal of iodine, 1 mL of dibromethane and 2 mL of neat p-bromo trifluoromethylbenzene to initiate the Grignard reaction. Following initiation of the reaction, the remainder of the p-bromotrifluoromethylbenzene (50 g, 0.22 mole total) in 100 mL dry tetrahydrofuran was added dropwise at a rate sufficient to maintain the reaction at gentle reflux. The addition took 1 hr. At the end of the addition period, the reaction mixture was heated to reflux for 3 hr. The reaction mixture was then cooled to room temperature and 10 mL water was added dropwise to coagulate the salts. The tetrahydrofuran was decanted and the remaining solids were slurried twice with 300 mL ethyl ether and twice with 300 mL dichloromethane. Each organic extract was decanted from the solids in turn and combined and evaporated under reduced pressure to an oil.

This oil was redissolved in 300 mL dichloromethane, washed once with 100 mL water and once with 10 mL saturated sodium chloride solution, dried and concentrated under reduced pressure. The resulting residue was distilled under reduced pressure (0.040 mm, 95°) to yield 2-(4,4-dimethyl-2-oxazoline-2-yl)-4'-trifluoromethylbiphenyl, yield 33%. A sample was recrystallized from 30°–60° petroleum ether (mp 50°–51°).

Elemental Analysis: Calculated for $C_{18}H_{16}F_3NO$: C, 67.70; H, 5.05; N, 4.39. Found: C, 67.62; H, 5.09; N, 4.39.

b. Preparation of 4'-(Trifluoromethyl)-2-biphenylcarboxylic acid

A solution of 2-(4,4-dimethyl-2-oxazolin-2-yl)-4'-trifluoromethylbiphenyl (3.5 g, 0.011 mole) in 60 mL 6N hydrochloric acid was stirred at vigorous reflux for 2 hr. The reaction mixture was then cooled to room temperature and extracted with methylene chloride. The organic extracts were dried and concentrated under reduced pressure to yield a solid. Recrystallisation from ethyl ether/pentane afforded 4'-(trifluoromethyl)-2-biphenyl carboxylic acid, yield 86% (mp 167°–169°).

Elemental analysis: Calculated for $C_{14}H_9F_3O_2$: C, 63.16; H, 3.41. Found: C, 63.12; H, 3.42.

TLC (lined tank), 10% methanol/chloroform, 1 spot $R_f$ 0.33, SILICA GEL 60 (trademark of Whatman Co., Clifton, N.J.) plate.

EXAMPLE 2

Preparation of 4-(n-Butyl)-2-biphenyl carboxylic acid a. Preparation of 2-(4,4-Dimethyl-2-oxazolin-2-yl)-4'-n-butylbiphenyl A mechanically stirred solution of magnesium turnings (Mallinckrodt, for Grignard's reaction, 3.75 g., 0.154 mole) and 2-(2-methoxyphenyl)-4,4-dimethyl-2-oxazoline (30 g, 0.146 mole) in 50 mL dry tetrahydrofuran under nitrogen was prepared. To this was added a crystal of iodine, 1 mL of dibromoethane and 2 mL of neat p-Iodo n-butylbenzene to initiate the Grignard reaction. After warming to initiate the reaction, the remainder of the p-iodo-n-butylbenzene (40 g, 0.154 mole) in 50 mL dry tetrahydrofuran was added dropwise at a rate sufficient to maintain the reaction at gentle reflux. The addition took 1 hr and the reaction mixture was then heated at reflux for 3 hr. The reaction was then cooled to room temperature and 15 mL water was added dropwise to coagulate the salts. The tetrahydrofuran was decanted and the remaining solids were slurried twice with 200 mL ethyl ether and twice with 300 mL dichloromethane. Each organic extract was decanted from the solids in turn and combined and evaporated under reduced pressure to an oil. The oil was redissolved in 300 mL dichloromethane, washed once with 100 ml saturated sodium chloride solution, dried and concentrated under reduced pressure. The resulting residue was distilled under reduced pressure (0.027 Torr, 130°) to yield 2-(4,4-dimethyl-2-oxazolin-2-yl)-4'-n-butylbiphenyl as an oil, yield 25%.

b. Preparation of 4'-(n-Butyl)-2-biphenylcarboxylic acid

A solution of 2-(4,4-dimethyl-2-oxazolin-2-yl)4'-n-butylbiphenyl (12 g, 0.039 mole) in 200 ml 6N hydrochloric acid was stirred at vigorous reflux for 48 hr. The reaction mixture was then cooled to room temperature and extracted with dichloromethane. The organic extracts were dried and concentrated under reduced pressure to yield an oil. Chromatography with an acetone/petroleum ether mixture yielded a solid. Recrystallization from acetone/petroleum ether afforded 4-(n-Butyl)-2-biphenylcarboxylic acid (yield 20%, mp 74°–76°).

Elemental analysis: Calculated for $C_{17}H_{18}O_2$: C, 80.28; H, 7.13. Found: C, 80.00; H, 7.15.

TLC (lined tank), 10% methanol/chloroform, 1 spot $R_f$ 0.48, SILICA GEL 60 plate.

EXAMPLE 3

Preparation of 2-(4-Biphenyl)benzoic acid a. Preparation of 2-(4,4-Dimethyl-2-oxazolin-2-yl)-4'-phenylbiphenyl

A mechanically stirred solution of magnesium turnings (Mallinckrodt, for Grignards reaction, 2.95 g, 0.12 mole) and 2-(2-methoxyphenyl)-4,4-dimethyl-2-oxazoline (23.4 g, 0.114 mole) in 100 mL dry tetrahydrofuran under nitrogen was prepared. To this was added a crystal of iodine, 1 mL of dibromoethane and 2 mL of neat p-bromophenylbenzene (also known as p-bromobiphenyl) to initiate the Grignard reaction. Following initiation of the reaction, the remainder of the p-bromophenylbenzene (28 g, 0.12 mole total) in 100 mL dry tetrahydrofuran was added dropwise at a rate sufficient to maintain the reaction of gentle reflux. The addition took 1 hr, at the end of which the reaction was heated to reflux for 4 hr and then allowed to stir overnight at room temperature. The reaction was then worked up by adding 15 mL water to the stirred mixture to coagulate the salts. The tetrahydrofuran was decanted and the remaining solids were slurried twice with 300 mL ethyl ether and twice with 300 mL dichloromethane. Each organic extract was decanted from the solids in turn and combined and evaporated under reduced pressure to an oil.

The oil was redissolved in 300 mL dichloromethane, washed once with 100 mL water and once with 100 mL saturated chloride solution, dried and concentrated under reduced pressure to an oil. The oil was chromatographed, eluting with ethyl acetate/petroleum ether to yield a solid. Recrystallization from acetone/petroleum ether afforded 2-(4,4-dimethyl-2-oxazolin-2-yl)-4'-phenyl-biphenyl (16% yield, m.p. 95°–97°).

b. Preparation of 2-(4-biphenyl)benzoic acid

A solution of 2-(4,4-dimethyl-2-oxazolin-2-yl)-4'-phenylbiphenyl (6.3 g, 0.019 mole) in 100 mL 6N hydrochloride acid was stirred at vigorous reflux for 24 hr. The reaction mixture was then cooled to room temperature and extracted with dichloromethane. The organic extracts were dried and concentrated under reduced pressure to yield an oil. Chromotography of the oil in acetone/petroleum ether yielded a solid. Recrystallization of the solid from acetone/petroleum ether afforded 2-(4-biphenyl)benzoic acid (yielded 28%, m.p. 194°–195°).

Elemental analysis: Calculated for $C_{19}H_{14}O_2$: C, 83.19; H, 5.14. Found: C, 83.19; H, 5.10

TLC (lined tank), 10% methanol/chloroform, 1 spot, $R_f$ 0.4, SILICA GEL 60 (Trade Name) plate.

EXAMPLE 4

Preparation of 4'-(Trifluoromethyl)-2-biphenyl carboxylic acid-alternate method a. Preparation of 2-Bromobenzaldehyde Dimethyl Acetal

A solution of 2-bromobenzaldehyde (451.9 g, 2.44 mol), trimethyl orthoformate (324 g, 3.05 mol) and concentrated hydrochloric acid (4.0 ml, 0.05 mol) in methanol (2 L) was refluxed for four hours. The volatile components were evaporated on the rotary evaporator and the residue dried over anhydrous potassium carbonate, filtered, and distilled (66°–72° C. at 0.1–0.2 mm) to give 474.1 g (84%) of the 2-Bromobenzaldehyde Dimethyl Acetal compound as a colorless oil. 'H NMR ($CDCl_3$): 3.35 (s, 6, $OCH_3$), 5.50 (s, 1, CH), 7.5 (m, 4, Ar—H).

b. Preparation of Iodo (4-trifluoromethylphenyl)-bis(triphenylphosphine) palladium (II)

To a slurry of tetrakis (triphenylphosphine) palladium (O) (12.61 L g, 10.9 mmol) in dry benzene (35 ml) under nitrogen was added a solution of 4-iodobenzotrifluride (2.97 g, 10.9 mmol) in benzene (35 mL). One hour after dissolution the solvent was evaporated and the residue triturated with cold diethyl ether. The Iodo(4-trifluoromethylphenyl)-bis(triphenylphosphine)palladium (II) compound (9.58 g, 97%) was filtered, dried in vacuo and stored in a brown bottle under nitrogen.

c. Preparation of 4'-Trifluoromethyl-2-biphenylcarbaldehyde

To magnesium turnings (1.23 g, 50.7 mmol) in a dry flask under nitrogen was added anhydrous tetrahydrofuran (THF, 10 mL). The mixture was mechanically stirred while a solution of 1,2-dibromoethane (1.22 g, 6.5 mmol) in THF (10 mL) was added dropwise. Upon completion, a solution of the dimethyl acetal of 2-bromobenzaldehyde (3.00 g, 13.0 mmol) and 1,2-dibromoethane (2.44 g, 13.0 mmol) in THF (10 ml) was added at a rate to maintain gentle reflux. Upon completing, a second solution of 1,2-dibromoethane (1.22 g, 6.5 mmol) in THF (10 mL) was added dropwise. The mixture was then refluxed an additional 20 minutes and decanted into an addition funnel attached to a second reaction flask containing a solution of 4-iodobenzotrifluoride (2.72 g, 10.0 mmol) and iodo(4-trifluoromethyl)bis(triphenylphosphine)palladium (II) (0.21 g, 0.9 mmol) in refluxing THF (20 mL). The Grignard reagent was added dropwise and the mixture refluxed for 1½ hr. After cooling to room temperature, 3N hydrochloric acid was added (30 mL) and the THF evaporated on the rotary evaporator. The residue was extracted with diethyl ether. The ether extract was washed with 3N hydrochloric acid (20 mL) water (4×25 mL), and saturated sodium chloride solution (10 mL). The ether solution was then dried ($MgSO_4$), treated with charcoal, filtered and evaporated to give a dark yellow oil (3.41 g). This was chromatographed on the Waters Prep 500 HPLC using a 1:1 mixture of methylene chloride and hexane. The product was isolated after evaporation of solvent as a light yellow oil (2.41 g, 96.4%). 'H NMR (CDCl₃): 7.6 (m, 7, Ar—H), 8.0 (m, 1, 3-H), 9.9 (s, 1, CHO).

Elemental analysis: calculated for $C_{14}H_9F_3O$: C, 67.20; H, 3.62. Found: C, 67.39; H, 3.69.

d. Preparation of 4'-Trifluoromethyl-2-biphenylcarboxylic acid

To a solution of 4'-Trifluoromethyl-2-biphenylcarbaldehyde (1.08 g, 4.32 mmol) in tert-butanol (15 mL) at 80° C. was added a solution of potassium permanganate (0.89 g, 5.62 mmol) in water (25 mL). After stirring at 80° C. for two hours, the mixture was cooled, a solution of 3N sodium hydroxide was added (2 mL) and the manganese dioxide was filtered off. The filtrate was diluted with water (15 mL) and acidified with 6N hydrochloric acid to precipitate the title compound (1.05 g, 91.2%). Dissolution in 0.3N sodium hydroxide (15 mL), followed by charcoal treatment, filtrating, and precipitation with 6N hydrochloric acid gave the purified 4-Trifluoromethyl-2-biphenylcarboxylic acid compound (0.85 g, 85%). 'H NMR (CDCl₃): 7.5 (m, 7, ArH), 8.0 (m, 1,3-H), 9.5 (broad s, 1, CO₂H).

EXAMPLE 5

By the method of Example 1, the following compounds were prepared:

2-(4-Bromophenyl)benzoic acid, m.p. 156°-158°;
2-(4-Methoxyphenyl)-benzoic acid, m.p. 145°-147°;
2-(4-Fluorophenyl)-benzoic acid, m.p. 130°-132°;
2-(4-Methylphenyl)-benzoic acid, m.p. 148°-150°;
2-(4-Chlorophenyl)-benzoic acid, m.p. 166.5°-167.5°;
2-(4-Ethylphenyl)-benzoic acid, m.p. 129°-131°;
2-(4-isoPropylphenyl)-benzoic acid, m.p. 106.5°-107.5°;
2-(4-t-Butylphenyl)-benzoic acid, m.p. 129°-131.5°;
1-(4-Trifluoromethylphenyl)-2-naphthoic acid, m.p. 227°-228.5°;
1-(4-Ethylphenyl)-2-naphthoic acid, m.p. 152°-154°; and
2-(2-Naphthyl)-benzoic acid, m.p. 191°-192°.

EXAMPLE 6

Effect of 2-(4-trifluoromethylphenyl)-benzoic acid in the hyperchloresterolemic male rat Hypercholesterolemia was produced in male rats after 3 days in a diet of 0.4% cholesterol and 0.2% sodium cholate. Each group contained 4 rats. Compounds tested were given orally twice daily for 3 days and once on day 4. Control animals received the vehicle, methyl cellulose. The cholesterol-containing diet and compound treatment were started at the same time. Animals were bled before dietary and compound treatment and 3 hr after the last dose of compound on day 4. All bleedings were after a 4 hr fast. Total serum cholesterol, triglyceride and high density lipoprotein (HDL) cholesterol determined by the procedure and test kit supplied by Dow Diagnostics (Trademark of the Dow Chemical Co. Laboratories, Indianapolis, IN.). Very low and low density lipoprotein (VLDL and LDL) cholesterol were determined by the difference between total and HDL cholesterol. Table I shows the effect of 2-(4-trifluoromethylphenyl)-benzoic acid and Clofibrate on serum total cholesterol and triglyceride levels. Table II shows the effect of 2-(4-trifluoromethylphenyl)benzoic acid and clofibrate on HDL and VLDL and LDL cholesterol.

TABLE I

Inhibition of dietary induced hypercholesterolemia

| Compound | Dose mg/kg/day | % change in serum from control Cholesterol | Triglyceride |
|---|---|---|---|
| IA(R = CF₃) | 150 | −40 | −60 |
| " | 100 | −51 | −57 |
| " | 100 | −56 | −53 |
| " | 25 | −40 | −43 |
| Clofibrate | 200 | −28 | −40 |
| " | 100 | 0 | −33 |
| " | 50 | 0 | −31 |
| " | 25 | 0 | 0 |

TABLE II

Effect on HDL and VLDL & LDL Cholesterol

| Compound | Dose mg/kg/day | % change in serum from control VLDL & LDL | HDL |
|---|---|---|---|
| I(R = CF₃) | 150 | −52 | −15 |
| " | 50 | −64 | +10 |
| " | 25 | −46 | −6 |
| Clofibrate | 200 | −29 | −28 |
| " | 100 | 0 | −21 |

EXAMPLE 7

Effect of compounds of formula (IA) on Cholesterol and Triglyceride levels in rats By the method of Example 5 various compounds of formula (IA) were assessed for their ability to reduce cholesterol and triglyceride levels in rats. The compound were compared in efficacy to clofibrate. The results are shown in Table (III).

TABLE (III)

| R in formulation (IA) | Cholesterol lowering | Triglyceride lowering |
|---|---|---|
| CF₃ | A | A |
| n C₄H₉ | A | A |
| OCH₃ | M | A |
| F | In | M |
| CH₃ | M | M |
| Cl | M | In |
| C₂H₅ | A | A |
| i C₃H₇ | A | A |
| t C₄H₉ | M | A |

Key: In = Inactive at dose tested
A = Activity > clofibrate
M = Activity ≤ clofibrate

EXAMPLE 8

Pharmaceutical Formulation a. Capsule

Compound of formula (I): 150.0 mg
Corn Starch: 45.0 mg
Stearic Acid: 12.0 mg
Lactose: 93.0 mg The finely divided Compound (I) is mixed with the powdered excipients lactose, corn starch, and stearic acid and filled into hard shell gelatin capsules.

b. Syrup

Compound (I) as Sodium Salt (equivalent to 150 mg of Free Acid): 162.4 mg
Glycerin: 500.0 mg
Sucrose: 3,500.0 mg
Flavouring Agent: q.s.

Colouring Agent: q.s.
Preserving Agent: 0.1%
Purified Water: q.s. to 5.0 ml

Compound (I) Sodium Salt and sucrose were dissolved in the glycerin and a portion of the purified water. The preserving agents were dissolved in another portion of hot purified water, and then the colouring agent was added and dissolved. The two solutions were mixed and cooled before the flavouring agent was added. Purified water was added to final volume. The resulting syrup was thoroughly mixed.

c. Tablet

Compound (I) Sodium Salt (equivalent to 150 mg of free acid): 162.4 mg
Corn Starch: 30.0 mg
Lactose: 87.6 mg
Magnesium Stearate: 3.0 mg
Polyvinylpyrrolidone: 6.0 mg
Stearic Acid: 12.0 mg Compound (I) Sodium Salt was finely ground and intimately mixed with the powdered excipients, corn starch and lactose. The powders were wetted with a solution of polyvinylpyrrolidone dissolved in purified water and denatured alcohol to form granules. The granules were dried and mixed with the powdered stearic acid and magnesium stearate. The formulation was then compressed into tablets weighing 300 mg each.

d. Tablet

Compound formula (I): 150.0 mg
Corn Starch: 30.0 mg
Lactose: 100.0 mg
Magnesium Stearate: 2.0 mg
Polyvinylpyrrolidone: 6.0 mg
Stearic Acid: 12.0 mg Compound (I) was finely ground and initimately mixed with the powdered excipients, corn starch and lactose. The powders were wetted with a solution of polyvinylpyrrolidone dissolved in purified water and denatured alcohol to form granules. The granules were dried and mixed with the powdered stearic acid and magnesium stearate. The formulation was then compressed into tablets weighing 300 mg each.

EXAMPLE 9

Toxicity

Oral administration of 2-(4-trifluoromethylphenyl)-benzoic acid to rats at upto 1 lg/kg bodyweight-no deaths were observed.

I claim:

1. 4'-Trifluoromethyl-2-biphenylcarbaldehyde.

* * * * *